(12) United States Patent
Faybishenko

(10) Patent No.: US 6,957,573 B2
(45) Date of Patent: Oct. 25, 2005

(54) VADOSE ZONE WATER FLUXMETER

(75) Inventor: Boris A. Faybishenko, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 10/353,414

(22) Filed: Jan. 28, 2003

(65) Prior Publication Data
US 2003/0140690 A1 Jul. 31, 2003

Related U.S. Application Data

(60) Provisional application No. 60/352,323, filed on Jan. 29, 2002.

(51) Int. Cl.$^7$ ............................................. E21B 49/00
(52) U.S. Cl. .................... 73/152.18; 73/73; 73/152.51; 73/152.55; 137/78.3
(58) Field of Search .............................. 73/152.18, 73, 73/152.51, 152.55, 76; 137/78.3

(56) References Cited

U.S. PATENT DOCUMENTS

| | | | | |
|---|---|---|---|---|
| 2,878,671 A | * | 3/1959 | Prosser et al. ................. | 73/73 |
| 3,961,753 A | * | 6/1976 | Sears ............................ | 73/73 |
| 5,941,121 A | * | 8/1999 | Faybishenko .................. | 73/73 |
| 5,969,242 A | * | 10/1999 | Hubbell et al. .......... | 73/152.51 |

* cited by examiner

Primary Examiner—Hezron Williams
Assistant Examiner—André K. Jackson
(74) Attorney, Agent, or Firm—Henry P. Sartorio; Joseph R. Milner

(57) ABSTRACT

A Vadose Zone Water Fluxmeter (WFM) or Direct Measurement WFM provides direct measurement of unsaturated water flow in the vadose zone. The fluxmeter is a cylindrical device that fits in a borehole or can be installed near the surface, or in pits, or in pile structures. The fluxmeter is primarily a combination of tensiometers and a porous element or plate in a water cell that is used for water injection or extraction under field conditions. The same water pressure measured outside and inside of the soil sheltered by the lower cylinder of the fluxmeter indicates that the water flux through the lower cylinder is similar to the water flux in the surrounding soil. The fluxmeter provides direct measurement of the water flow rate in the unsaturated soils and then determines the water flux, i.e. the water flow rate per unit area.

11 Claims, 5 Drawing Sheets

Water Cell with Controlling Tensiometer

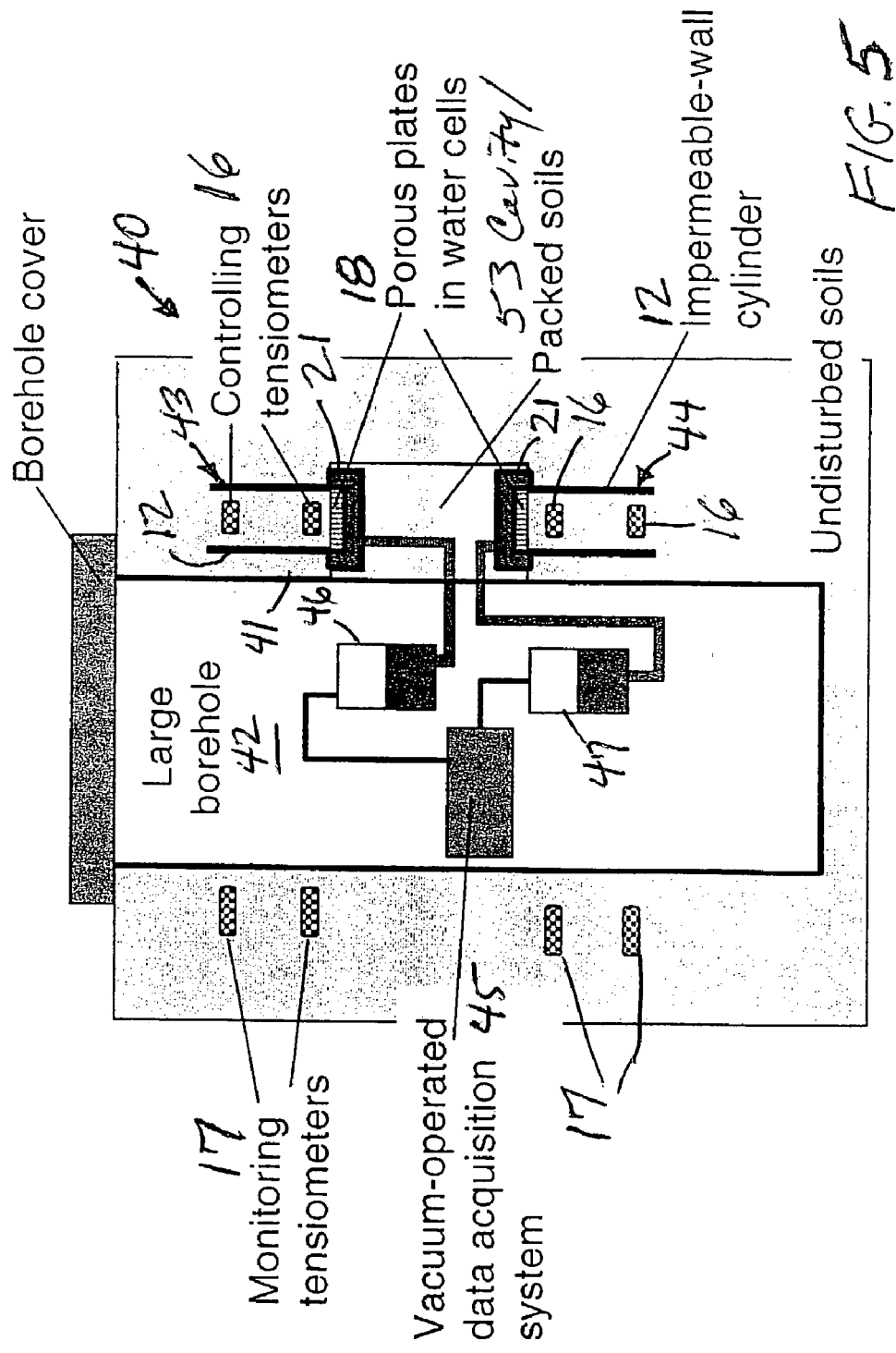

VADOSE ZONE WATER FLUXMETER

RELATED APPLICATIONS

This application claims priority of Provisional Application Ser. No. 60/352,323 filed Jan. 29, 2002, which is herein incorporated by reference.

GOVERNMENT RIGHTS

The United States Government has rights in this invention pursuant to Contract No. DE-AC03-76SF00098 between the United States Department of Energy and the University of California.

BACKGROUND OF THE INVENTION

The invention relates to underground geophysical/hydrogeologic measurements, and more particularly to direct measurement of unsaturated water flow in the soils of the vadose zone.

The vadose zone is the zone between the soil surface and the first regional water table. The water flow in the vadose zone is unsaturated.

For a variety of applications, including soil physics, soil chemistry, agriculture, remediation, hydrogeology, and hydrology, it is desirable to measure unsaturated water flow in comprising unconsolidated soils and sediments of the vadose zone. Current systems rely on derived calculations performed using thermal properties, hydraulic conductivity, or vertical moisture content profiles. Other direct systems require trenches, large lysimeters, or large boreholes, which disturb the soil and alter its properties.

It is further desirable to provide direct field measurement of water velocity and chemical fluxes at different depths in the vadose zone. These measurements yield in situ information on water flux and chemical transport through the vadose zone into the groundwater, can be used to calibrate mathematical models and numerical codes, and can also be used to monitor and control the effectiveness of remediation or agricultural procedures.

Accordingly, it is desirable to provide an improved direct measurement of unsaturated water flow in the vadose zone. It is also useful in some cases to determine other hydraulic soil parameters such as unsaturated hydraulic conductivity.

SUMMARY OF THE INVENTION

The invention is a Vadose Zone Water Fluxmeter (WFM) or Direct Measurement WFM, and method using the WFM, for providing direct measurement of unsaturated water flow in the vadose zone. The fluxmeter is a cylindrical device that fits in a borehole or can be installed near the surface, or in pits, or in pile structures, or in a trench. The fluxmeter is primarily a combination of tensiometers and a porous element or plate in a water cell that is used for water injection or extraction under field conditions. The fluxmeter is a cylinder with two parts, an upper cylinder and a lower cylinder, separated by a water cell. (The upper cylinder can be eliminated in some configurations.)

The lower or confining cylinder is pushed into the soil to create a sheltered zone of soil that is not influenced by water flow in the surrounding soil. Two tensiometers, an external or monitoring tensiometer outside the lower cylinder and an internal or controlling tensiometer inside the lower cylinder, are inserted into the soil. The same water pressure measured outside and inside of the soil sheltered by the lower cylinder of the fluxmeter indicates that the water flux through the lower cylinder is similar to the water flux in the surrounding soil. The fluxmeter provides direct measurement of the water flow rate (FR) in the unsaturated soils, which then is used to determine the water flux (WF), i.e. the water flow rate per unit area.

A dual fluxmeter system is designed for installation in the side wall of a borehole or trench. Additional tensiometers can be used to determine other parameters.

BRIEF DESCRIPTION OF THE DRAWINGS

FIG. 5 illustrates a dual fluxmeter system installed in the side wall of a borehole.

DETAILED DESCRIPTION OF THE INVENTION

The Vadose Zone Water Fluxmeter (WFM) or Direct Measurement WFM of the invention is a device for providing direct measurement of unsaturated water flow in the unconsolidated soils and sediments of the vadose zone. Performance of this device was evaluated by testing an analogous device under field conditions and by numerical simulations of the capability of direct measurement of unsaturated water flow in soil.

The fluxmeter is a cylindrical device intended to fit in a 4 inch to 6 inch diameter borehole. The fluxmeter can also have a larger diameter if used in larger boreholes or installed near the surface, or in pits, or in pile structures. The fluxmeter is primarily a combination of tensiometers and a porous element or plate in a water cell that is used for water injection or extraction under field conditions. A tensiometer is a device commonly used to measure water pressure in soil and to determine the direction of water flow in a soil profile. An illustrative tensiometer that is used in a preferred embodiment of the invention is described in U.S. Pat. No. 5,941,121, which is herein incorporated by reference. The purpose of the fluxmeter is to provide direct measurement of the water flow rate (FR) in the unsaturated soils and then determine the water flux (WF), i.e. the water flow rate per unit area.

Figure 1:
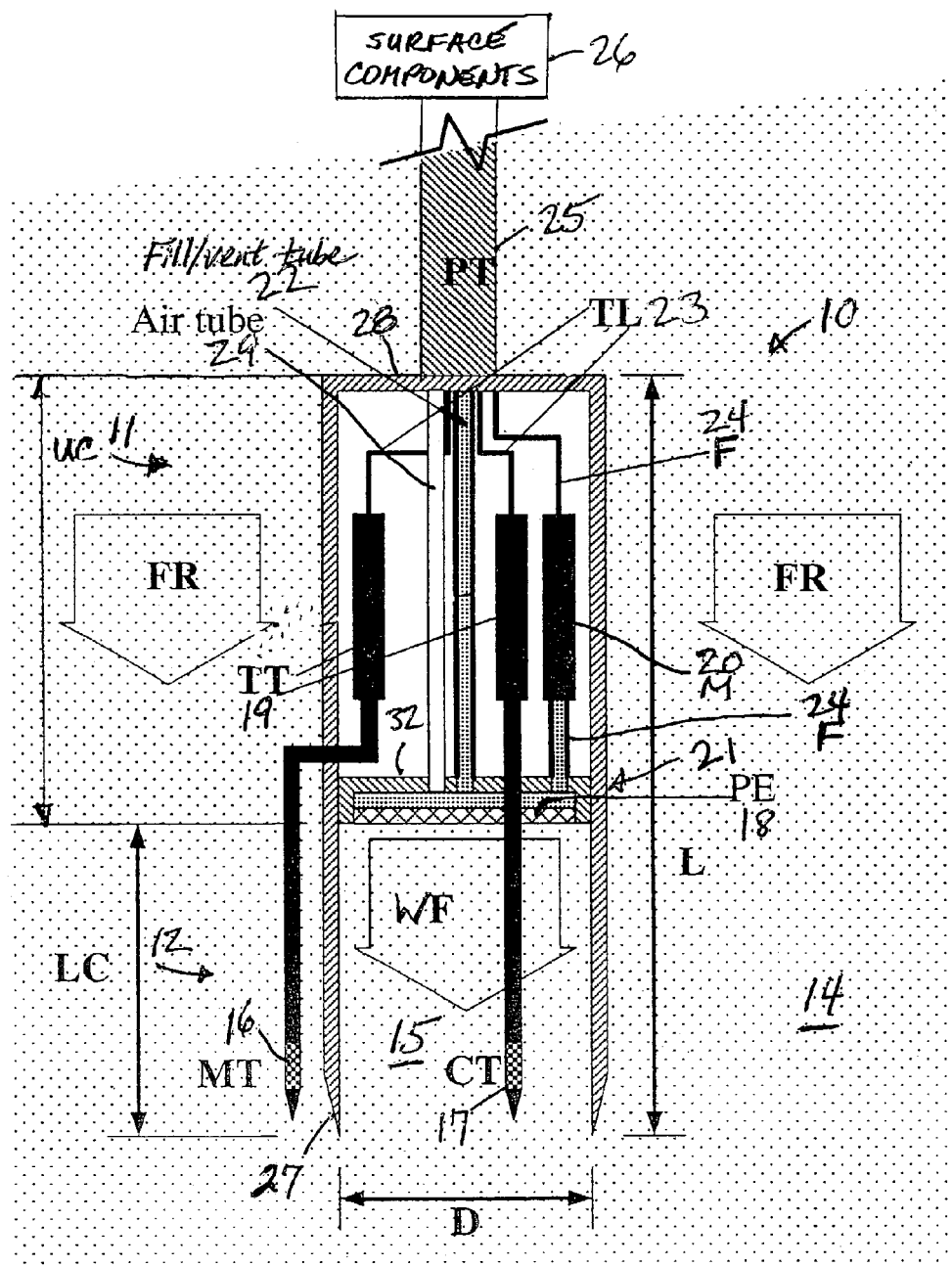
FIG. 1 is a cross sectional view of a fluxmeter of the invention inserted in soil.

The principal elements and general configuration of the fluxmeter are shown in FIG. 1. Fluxmeter 10 is a cylinder with two parts, upper cylinder (UC) 11 and lower or confining cylinder (LC) 12. The fluxmeter 10 is designed so that the lower cylinder (LC) is pushed into the soil 14 to create a sheltered zone 15 of soil that is not influenced by water flow in the surrounding soil. With LC 12, two tensiometers (a monitoring tensiometer (MT) 16 outside LC 12 and a controlling tensiometer (CT) 17 inside LC 12) are inserted into the soil 14. (Upper cylinder 11 is optional in some configurations.)

In the case of a borehole installation, the fluxmeter would be pushed into the soil at the bottom of the borehole. Upon insertion, the borehole would be back filled. An alternative installation approach may be used for applications in a built up pile structure of soil-like material (such as the mining heap leaching application). In this alternative installation approach, the pile structure would be built to an intermediate level where the water flux measurements are needed. At this level, the lower portion of the fluxmeter would be pushed into the material. The pile structure would then continue to be built up, burying the fluxmeter.

The main elements of the fluxmeter 10 are the external (monitoring) and internal (controlling) tensiometers (MT and CT) 16, 17 and the porous element or plate (PE) 18 through which water is either injected into the soils in the lower cylinder 12 (if flow is downward) or extracted from the soils in the lower cylinder 12 (if flow is upward). PE 18 is part of water cell 21, which separates UC 11 from LC 12. The flow rate measurements are obtained by regulating the flow to (from) porous element (PE) 18 so that the soil water pressure measured by controlling tensiometer (CT) 17 within the soil sheltered by lower cylinder (LC) 12 is substantially the same as the water pressure measured by monitoring tensiometer (MT) 16 outside of LC 12.

The same water pressure measured outside and inside of the soil sheltered by the lower cylinder indicates that the water flux (WF) through the lower cylinder is similar to the water flux in the surrounding soil. By dividing the water flow rate through the porous element by the cross sectional area of the device (a function of the porous plate diameter), the water flux in the surrounding soil can be computed.

The fluxmeter typically has a diameter of D=3 to 4 inches or larger depending on the type of installation. (An increase in the diameter increases the accuracy of measurements.) Tensiometer transducers (TT) 19 and the water-measuring element (M) 20 are located just above the porous element (PE) 18 inside of the upper protective cylinder (UC) 11. Fill and vent tubing 22, pressure transducer lines (TL) 23 from the tensiometers, and porous element feed/extraction line (F) 24 extend to the soil surface. Measuring element (M) 20 is located in feed/extraction line (F) 24 which extends from water cell 21 to the surface. The tensiometers, feed line, and the water measuring element can be operated remotely from the surface using special solenoids connected to a computer-based data acquisition system.

The upper cylinder 11 may continue to the surface or, as an alternative, as shown, the upper cylinder may have an enclosed top 28, with a protective tube (PT) 25 enclosing the fill and vent tubing, pressure transducer signal lines, and porous element feed and extraction line, which extend up to the soil surface. The length (L) from the bottom of the fluxmeter to the enclosed top is typically between 12 and 18 inches.

Surface components 26 of the fluxmeter at the soil surface are shown generally in FIG. 1 and are not described in detail herein. These components include a reservoir or water supply system for the water injection/extraction element, controls for regulating the flow to/from the water injection/extraction element (based on moisture level indications from the two tensiometers), and instrumentation indicating the feed water flow rate to/from the water injection/extraction element.

The Vadose Zone Water Fluxmeter is installed in a borehole (typically from 3 to 6 inches in diameter) of any depth, and it accurately and directly measures water flow through unsaturated vadose zone soils. Concentration flux can also be obtained from measurements of the concentration of dissolved chemicals in water in the fluxmeter. The bottom edge 27 of LC 12 is preferably sharpened to facilitate insertion into the soil.

Figure 2:
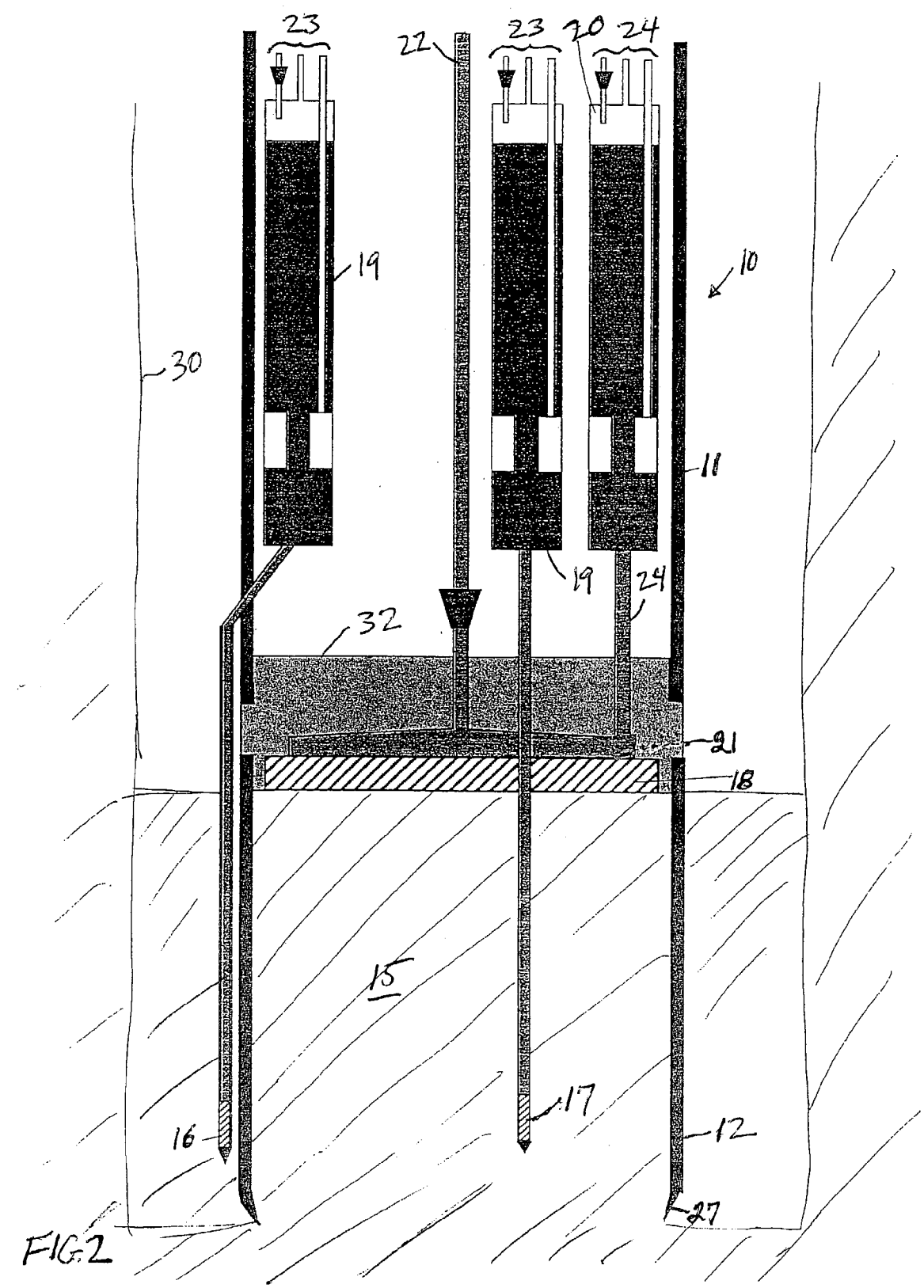
FIG. 2 is another cross sectional view of the fluxmeter in a borehole.

FIG. 2 shows a fluxmeter 10 positioned in a borehole 30. Confining cylinder 12 has a sharpened bottom edge 27 for ease of insertion into the soil at the bottom of the borehole.

The porous plate 18 located in the water cell 21 covers the top of the confining cylinder 12. Porous plate 18 can be fabricated from ceramic or sintered stainless steel material. The connection between the porous plate and the cylinder is watertight. Controlling tensiometer 17 is inserted through the top cover 32 of water cell 21 (and of lower cylinder 11). Tensiometer 17 has a drive point at its bottom tip. Tensiometer 17 is used to measure the water pressure within the semi-confined soil 15 inside the cylinder 12 to regulate the water flux through plate 18 so that the pressure measured by tensiometer 17 is the same as that measured by tensiometer 16 outside the cylinder 12. A water flux measuring device 20 operating on the Mariotte principle is located in the upper cylinder 11. Tube 22 is used to remove entrapped air and infill the water cell 21 as needed.

Figure 3:
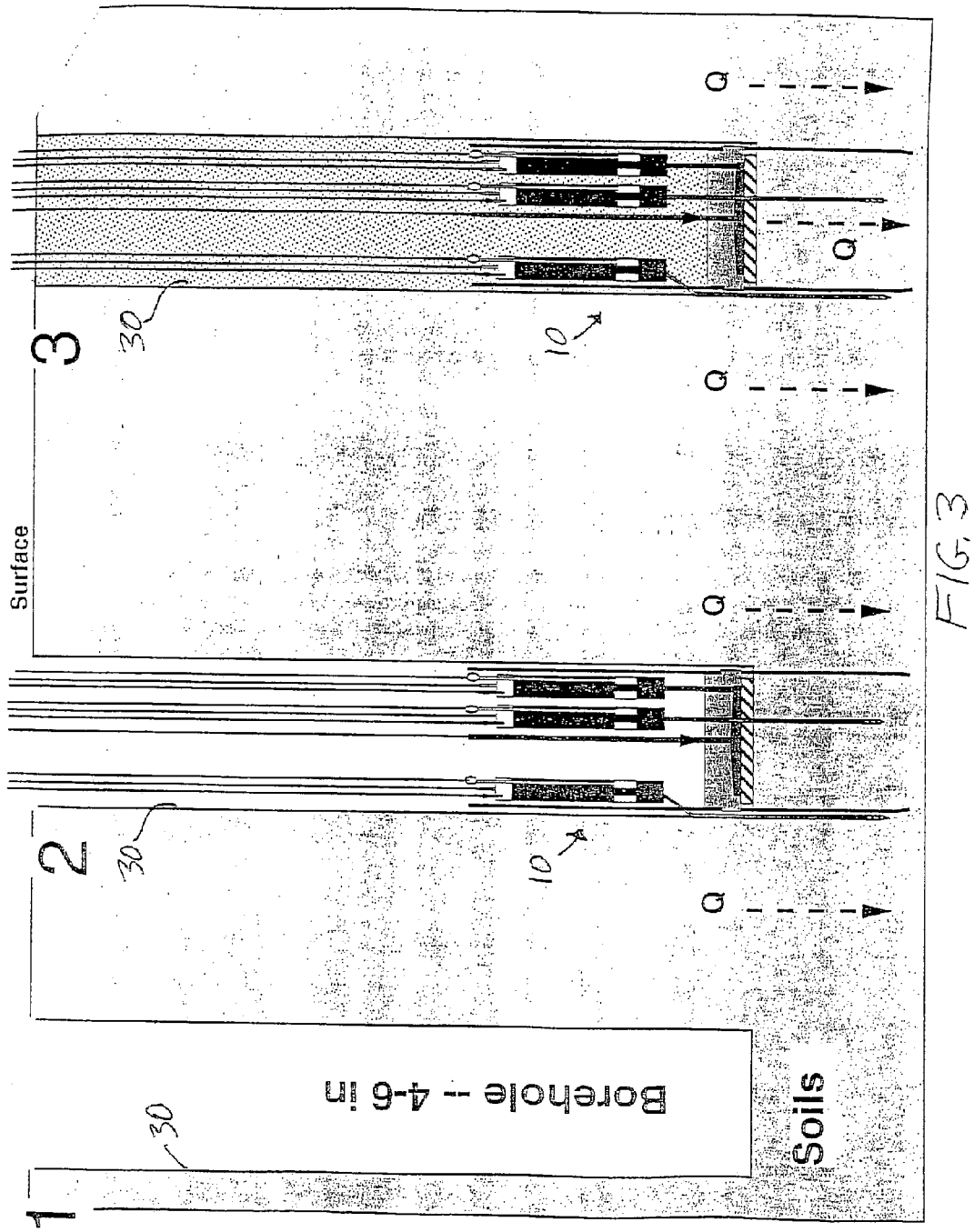
FIG. 3 illustrates the installation of a fluxmeter into a borehole.

Once the fluxmeter is installed in the borehole, the rest of it may be backfilled with soil or impermeable material. FIG. 3 shows three boreholes: #1 empty (before fluxmeter is installed), #2 with fluxmeter installed at bottom, and #3 with fluxmeter installed and backfilled.

To operate, the semi-confined lower cylinder is inserted into the soil until the porous plate contacts the soil. This lower cylinder shelters the soil in which water flux is measured by the fluxmeter. The controlling and monitoring tensiometers measure the moisture conditions inside and outside the cylinder. The flux through the porous plate is controlled until the pressures measured by the two tensiometers is about equal. When the pressures inside and outside the confining cylinder are equal, the flux through the porous plate equals the flux through the soil. Since the flow rate and area of the porous plate are known, the flux outside the cylinder can be determined.

Figure 4:
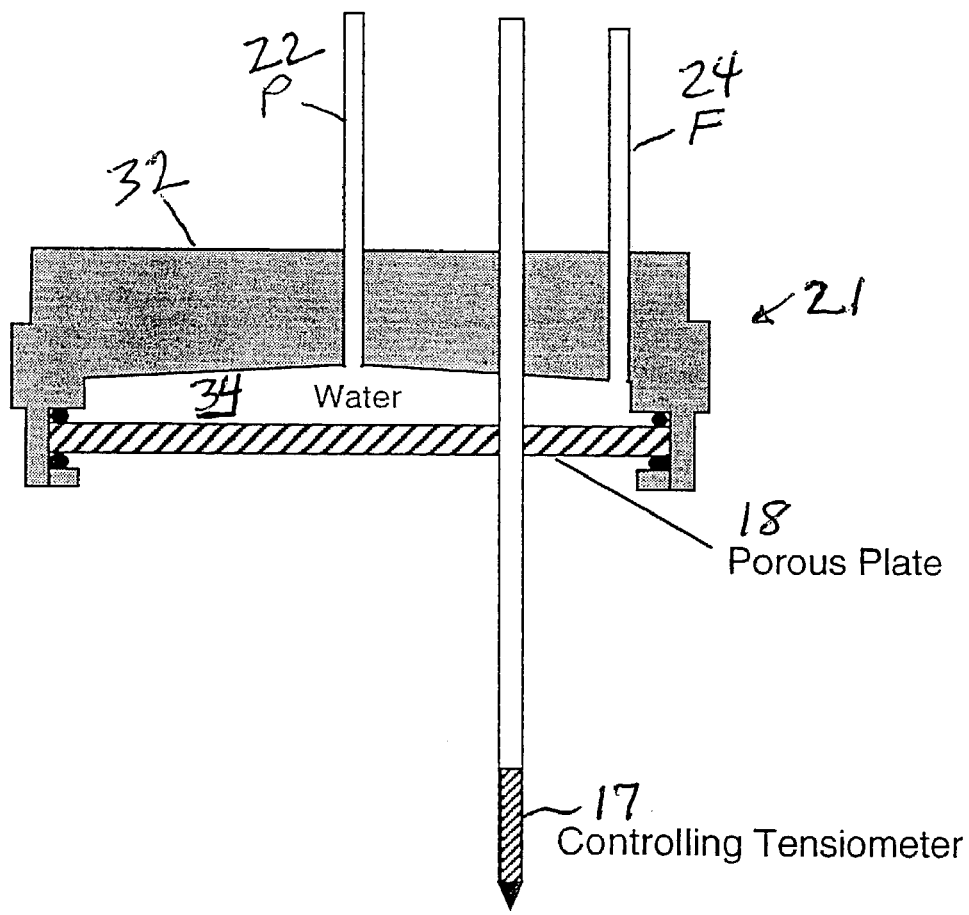
FIG. 4 shows the water cell and controlling tensiometer of the fluxmeter.

FIG. 4 shows the water cell 21 with controlling tensiometer 17. The porous plate 18 allows water to exit (or enter) the water chamber 34 in the cell. The inlet/outlet porous element feedline (F) 24 from the water measuring element controls water flow into/out of the water cell 21 during operation. The purge line (P) 22 is used to purge the cell (of air or water), but is closed during cell operation. A separate air vent 29 may also be included as shown in FIG. 1. Water cell 21 and associated water measuring element 20 allow the measurement of the actual flow rate inside lower cylinder 12, whether the flow is produced by injecting water down into the lower cylinder through porous plate 18 or by extracting the natural water flowing in the soil upward into lower cylinder 12.

FIG. 5 illustrates a dual fluxmeter system 40 installed in the side wall 41 of a large borehole (or trench) 42. System 40 includes a pair of fluxmeters 43, 44 similar to that previously described except that there is no upper cylinder. One fluxmeter 43 is installed facing up (upper cell) and the other fluxmeter 44 faces down (lower cell). Each fluxmeter has a porous plate 18 in a water cell 21 at one end. A pair of controlling tensiometers 16 are positioned inside impermeable wall cylinders 12 of each fluxmeter 43, 44, and an associated pair of monitoring tensiometers 17 are positioned in the soil outside each of cylinders 12. The pairs of controlling and monitoring tensiometers 16, 17 are used to obtain other hydraulic parameters of the soils, such as unsaturated hydraulic conductivity. (A single tensiometer can be used for each of the pairs if only water flow rate is desired. Additional tensiometers can be added to fluxmeter 10 of FIG. 1 to determine other parameters.) Cavity 53 in borehole (or trench) side wall 41 is filled with packed soil after installation of fluxmeters 43, 44.

The operation of the system is controlled by a data acquisition system 45, shown positioned in the borehole (but alternately positionable on the surface), connected through the water supplies 46, 47 to the two cells 43, 44. In the case of downward flow, the upper cell 43 is used to extract water, and the lower cell 44 is used to inject water. In the case of upward flow, the lower cell 44 is used to extract water, and the upper cell 43 is used to inject water. When the same amount of water is supplied into the opposite porous plate, a natural flow pattern is preserved. The operation of the system is similar to the above, where the measured flow rate in the water cells yields the water flux in the soil.

Benefits

Measurements can be taken at any depth with reduced errors of up to 90% compared to current systems. The Direct Measure WFM can be utilized in vertical or slanted boreholes, all while maintaining borehole integrity. The measurements can be taken in real time to determine solute flux variability and calculate hydraulic parameters of soils such as unsaturated hydraulic conductivity, based on measurements using pairs of controlling and monitoring tensiometers.

Applications

This device provides data of fluid flow and concentration flux for soil physics, soil chemistry, agriculture, remediation, hydrogeology, and hydrology applications. Liquid spill measurements and monitoring, including pore solution sampling can also be conducted.

Changes and modifications in the specifically described embodiments can be carried out without departing from the scope of the invention which is intended to be limited only by the scope of the appended claims.

What is claimed is:

1. A method for measuring water flow in soil, comprising:
    providing a fluxmeter, comprising:
        a lower cylinder open at one end thereof,
        a water cell mounted at the opposed end of the lower cylinder,
        a porous plate in the water cell and communicating with the lower cylinder,
        a controlling tensiometer mounted within the lower cylinder, and
        a monitoring tensiometer mounted outside the lower cylinder;
    inserting the fluxmeter into the soil so that the interior of the lower cylinder is isolated from the water flow in the surrounding soil:
    measuring the water pressure at the controlling and monitoring tensiometers;
    controlling the flow of water into or out of the lower cylinder through the porous plate until the measured water pressures at the controlling and monitoring tensiometers are substantially equal;
    determining the water flux in the soil from the water flow rate through and area of the porous plate.

2. The method of claim 1 wherein the fluxmeter is inserted in a borehole.

3. The method of claim 2 wherein the borehole is back filled after insertion of the fluxmeter.

4. The method of claim 1 wherein the fluxmeter is inserted near the soil surface, in a trench, in a pit, or in a pile structure.

5. The method of claim 1 wherein water is injected into the lower cylinder through the porous plate of the water cell when the water flow in the soil is downwards.

6. The method of claim 1 wherein water Is extracted from the lower cylinder through the porous plate of the water cell when the water flow in the soil is upwards.

7. A fluxmeter system, comprising:
    a pair of opposed fluxmeters, one (upper cell) facing up and the other (lower cell) facing down, each fluxmeter comprising:
        an impermeable wall cylinder;
        a water cell mounted at one end of the cylinder;
        a porous plate in the water cell and communicating with the cylinder;
        at least one controlling tensiometer inside the cylinder;
        at least one monitoring tensiometer outside the cylinder;
        a water supply controlling element connected to the water cell for controllably injecting water to or extracting water from the cylinder through the porous plate;
    a data acquisition system connected to the water supply controlling element of each fluxmeter.

8. The fluxmeter system of claim 7 wherein the fluxmeters are installed in the side wall of a borehole or trench.

9. The fluxmeter system of claim 8 wherein the upper cell is used to extract water through its porous plate and the lower cell is used to inject water through its porous plate when the water flow in the soil is downwards.

10. The fluxmeter system of claim 8 wherein the upper cell is used to inject water through its porous plate and the lower cell is used to extract water through its porous plate when the water flow in the soil is upwards.

11. The fluxmeter system of claim 7 wherein each fluxmeter has a pair of controlling tensiometers inside the cylinder and a pair of monitoring tensiometers outside the cylinder.

* * * * *